US007820639B2

(12) United States Patent
Lindstrom

(10) Patent No.: US 7,820,639 B2
(45) Date of Patent: Oct. 26, 2010

(54) OPHTHALMIC COMPOSITIONS INCLUDING LUBRICANT, DETURGESCENT AGENT, AND GLYCOSAMINOGLYCAN AND METHODS OF USING THE SAME

(76) Inventor: Richard L. Lindstrom, 2811 Westwood Rd., Wayzata, MN (US) 55931

( * ) Notice: Subject to any disclaimer, the term of this patent is extended or adjusted under 35 U.S.C. 154(b) by 1249 days.

(21) Appl. No.: 11/240,000

(22) Filed: Sep. 30, 2005

(65) Prior Publication Data

US 2006/0079482 A1   Apr. 13, 2006

Related U.S. Application Data

(60) Provisional application No. 60/643,860, filed on Jan. 14, 2005, provisional application No. 60/615,281, filed on Oct. 1, 2004.

(51) Int. Cl.
*A61K 31/715* (2006.01)
*A61K 31/70* (2006.01)
*A61K 47/00* (2006.01)

(52) U.S. Cl. .............................. 514/54; 514/59; 514/62; 514/912; 514/915

(58) Field of Classification Search .................. 514/54, 514/59, 62, 912, 915
See application file for complete search history.

(56) References Cited

U.S. PATENT DOCUMENTS

| 4,486,416 | A | 12/1984 | Soll et al. |
| 4,695,536 | A | 9/1987 | Lindstrom et al. |
| 4,696,917 | A | 9/1987 | Lindstrom et al. |
| 4,713,375 | A | 12/1987 | Lindstrom et al. |
| 4,725,586 | A | 2/1988 | Lindstrom et al. |
| 4,886,786 | A | 12/1989 | Lindstrom et al. |
| 5,013,714 | A | 5/1991 | Lindstrom et al. |
| 5,104,787 | A | 4/1992 | Lindstrom et al. |
| 5,204,325 | A | 4/1993 | Lindstrom et al. |
| 5,366,964 | A | 11/1994 | Lindstrom et al. |
| 5,407,669 | A | 4/1995 | Lindstrom et al. |
| 5,639,796 | A | 6/1997 | Lee |
| 5,728,405 | A | 3/1998 | McDonnell |
| 6,429,227 | B1 * | 8/2002 | Schneider et al. ........... 514/530 |
| 6,572,849 | B2 * | 6/2003 | Shahinian, Jr. ........... 424/78.04 |
| 6,878,694 | B2 | 4/2005 | Doshi et al. |
| 6,919,321 | B2 | 7/2005 | Wang et al. |
| 2002/0081289 | A1 | 6/2002 | Neuhann |
| 2003/0180262 | A1 | 9/2003 | Wironen et al. |
| 2003/0198630 | A1 | 10/2003 | Neuhann |

FOREIGN PATENT DOCUMENTS

| EP | 0 572 272 | 8/1999 |
| WO | WO 95/20969 | 8/1995 |
| WO | WO 01/56475 | 8/2001 |

OTHER PUBLICATIONS

Van Santvliet et al (Europen Journal of Pharmaceutical Sciences, "Influence of the physioco-chemical properties of ophthalmic viscolysers on the weight of drops dispensed from a flexible dropper bottle", 7(1999) p. 339-345).*
Arndt, Carmen, et al. "Preservation of canine and feline corneoscleral tissue in Optisol® GS", Veterinary Ophthalmology, 2001, pp. 175-182, vol. 4, No. 3.
Dogru M. e al. "Corneal sensitivity and ocular surface changes following preserved amniotic membrane transplantation for nonhealing corneal ulers", Eye, 2003, pp. 139-148, vol. 17.

* cited by examiner

*Primary Examiner*—Shaojia Anna Jiang
*Assistant Examiner*—Everett White
(74) *Attorney, Agent, or Firm*—Hugh D. Jaeger, Esq.

(57) ABSTRACT

Ophthalmic compositions are provided that include a lubricant, a deturgescent agent, a glycosaminoglycan, and water. Methods of using the ophthalmic compositions are also provided.

20 Claims, No Drawings

OPHTHALMIC COMPOSITIONS INCLUDING LUBRICANT, DETURGESCENT AGENT, AND GLYCOSAMINOGLYCAN AND METHODS OF USING THE SAME

This application claims the benefit of U.S. Provisional Application No. 60/643,860, filed Jan. 14, 2005, and U.S. Provisional Application No. 60/615,281, filed Oct. 1, 2004; the entire contents of these applications are hereby incorporated herein by reference.

FIELD

The invention generally relates to ophthalmic compositions including a lubricant, a deturgescent agent, and a glycosaminoglycan as well as to methods of using such ophthalmic compositions.

BACKGROUND

Various compositions utilizing a glycosaminoglycan such as chondroitin sulfate are known. For example, U.S. Pat. No. 4,486,416 relates to a method of protecting both human and animal endothelial and epithelial cells which are subject to exposure to trauma, and more particularly to protecting endothelial and epithelial cells in anticipation of surgical trauma using chondroitin sulfate.

U.S. Patent Application Publication Nos. 2002/0081289 and 2003/0198630 relate to an ophthalmic medicament which contains in aqueous solution or suspension at least one carbohydrate, at least one amino acid, at least one electrolyte, a chondroitin sulfate, and optionally further customary excipients. The publications state that the ophthalmic medicament can be employed in a large number of eye diseases and in particular in accompaniment to corneal transplantation and in refractive corneal surgery.

SUMMARY

In one aspect, an ophthalmic composition is provided that comprises glycerol in a concentration of from 0.1% to 5.0%, dextran in a concentration of from 0.1% to 10.0%, chondroitin sulfate in a concentration of from 0.1% to 5.0%, and water.

In another aspect, an ophthalmic composition is provided that consists essentially of glycerol in a concentration of from 0.1% to 5.0%, dextran in a concentration of from 1.0% to 10.0%, chondroitin sulfate in a concentration of from 0.1% to 5.0%, and water.

In a further aspect, an ophthalmic composition is provided that consists of glycerol in a concentration of from 0.1% to 5.0%, dextran in a concentration of from 1.0% to 10.0%, chondroitin sulfate in a concentration of from 0.1% to 5.0%, water, a buffer, and a tonicity modulating agent.

In yet a further aspect, an ophthalmic composition is provided that consists of glycerol in a concentration of from 0.1% to 5.0%, dextran in a concentration of from 1.0% to 10.0%, chondroitin sulfate in a concentration of from 0.1% to 5.0%, and water.

In yet another aspect, a method of treating corneal edema is provided. The method comprises administering to a cornea of a subject suffering from or susceptible to corneal edema an effective amount of an ophthalmic composition comprising glycerol in a concentration of from 0.1% to 5.0%, dextran in a concentration of from 1.0% to 10.0%, chondroitin sulfate in a concentration of from 0.1% to 5.0%, and water.

DETAILED DESCRIPTION

The present invention relates to ophthalmic compositions as well as methods of using the same.

The ophthalmic compositions of the present invention comprise a lubricant, a deturgescent agent, a glycosaminoglycan, and water. The lubricant is preferably glycerol, although other lubricants may be used, including, but not limited to, hydroxypropylmethyl cellulose, carboxy propylmethyl cellulose, sorbitol, polyvinyl pyrrolidone, polyethylene glycol, polyvinyl acetate, and combinations thereof.

The deturgescent agent is preferably dextran, although other deturgescent agents may be used including, but not limited to, dextran sulfate, NaCl, dextrose, sucrose, other sugars, and combinations thereof. Any suitable molecular weight dextran or mixture thereof may be used, including dextran 40, dextran 70, and/or dextran 500.

The glycosaminoglycan is preferably chondroitin sulfate, although other glycosaminoglycans (or other protective coating agents) may be used including, but not limited to, chondroitin, dermatan sulfate, dermatin sulfate, heparin sulfate, heparan sulfate, keratin sulfate, keratan sulfate, hyaluronic acid, and mixtures thereof. Any one isomer or salt of the glycosaminoglycan may be used, or a mixture of isomers and/or salts of the glycosaminoglycan may be used. For example, as used herein, "chondroitin sulfate" includes any type of chondroitin sulfate, including isomers and salts thereof as well as mixtures of isomers and/or salts thereof.

In some embodiments, the ophthalmic composition consists essentially of a lubricant, a deturgescent agent, a glycosaminoglycan, and water. The compositions may also include a buffer (e.g., buffers including citrates, phosphates, borates, bicarbonates, sodium salts, potassium salts, etc.), an acid or base to modify pH, a tonicity modulating agent (e.g., NaCl), and/or an antioxidant/free radical scavenger (e.g., ascorbate, ascorbic acid, glutathione, etc.). In other embodiments, the ophthalmic compositions consist of a lubricant, a deturgescent agent, a glycosaminoglycan, water, a buffer, and a tonicity modulating agent. In yet other embodiments, the ophthalmic compositions consist of a lubricant, a deturgescent agent, a glycosaminoglycan, and water.

The ophthalmic composition typically comprises an aqueous solution including a lubricant in a concentration of from 0.05% to 10.0%, a deturgescent agent in a concentration of from 0.1% to 20%, a glycosaminoglycan in a concentration of from 0.05% to 10.0%, and water (as used herein, "concentration" of a component of an ophthalmic composition means concentration based on mass of the component per total volume of the composition (i.e., mg/100 mL), and is typically expressed as a percentage).

In a preferred embodiment, the ophthalmic composition includes glycerol, dextran, chondroitin sulfate, and water. The glycerol is typically present in such a composition in a concentration of from 0.1% to 5.0%, preferably from 0.3% to 1.7%, more preferably from 0.6% to 1.4%, even more preferably from 0.8% to 1.2%, and even more preferably in a concentration of 1.0%. Dextran is typically present in such a composition in a concentration of from 0.1% to 10%, preferably from 0.5% to 10%, more preferably from 1.0% to 10.0%, more preferably from 3% to 7%, even more preferably from 4% to 6%, yet even more preferably from 4.5% to 5.5%, and even more preferably in a concentration of 5.0%. Chondroitin sulfate is typically present in such a composition in a concentration of from 0.1% to 5.0%, preferably from 0.5% to 4.5%, more preferably from 1.5% to 3.5%, even more preferably from 2.0% to 3.0%, even more preferably 2.3% to 2.7%, and even more preferably in a concentration of 2.5%.

The ophthalmic compositions typically have a pH from 5.0 to 9.0, preferably from 6.0 to 8.0, more preferably from 7.0 to 7.4, and even more preferably 7.0, although the compositions may also have a pH outside of these ranges. A buffer (e.g., a buffer with intrinsic antimicrobial properties such as a sodium borate/boric acid buffer) may be used to achieve (and maintain) the desired pH of the compositions, and/or an acid or base may be added to adjust the pH of the compositions to the desired level. Buffers that do not require adjustment of the pH of the compositions with additional acid or base are preferred.

The ophthalmic compositions typically have an osmolarity of from 100 to 500 milliosmoles/liter (mOsm/L), preferably from 150 to 450 mOsm/L, and more preferably from 200 to 400 mOsm/L, although the compositions may also have an osmolarity outside of these ranges. As mentioned above, a tonicity modulating agent such as sodium chloride may also be used in the compositions.

As stated above, in some embodiments, the ophthalmic composition comprises glycerol, dextran, chondroitin sulfate, and water, and optionally includes a buffer, an acid or base, a tonicity modulating agent, and/or a free radical scavenger. In other embodiments, the ophthalmic composition consists essentially of glycerol, dextran, chondroitin sulfate, and water, and optionally includes a buffer, an acid or base, a tonicity modulating agent, and/or a free radical scavenger. In further embodiments, the composition consists of glycerol, dextran, chondroitin sulfate, and water, and optionally includes a buffer, an acid or base, a tonicity modulating agent, and/or a free radical scavenger. In yet other embodiments, the composition consists of glycerol, dextran, chondroitin sulfate, and water.

In one particularly preferred embodiment, the ophthalmic composition comprises glycerol in a concentration of from 0.1% to 5.0%, dextran in a concentration of from 1.0% to 10.0%, chondroitin sulfate in a concentration of from 0.1% to 5.0%, and water, and optionally includes a buffer, an acid or base, a tonicity modulating agent, and/or a free radical scavenger. The pH of such a composition is preferably from 6.0 to 8.0.

In another preferred embodiment, the ophthalmic composition consists essentially of glycerol in a concentration of from 0.1% to 5.0%, dextran in a concentration of from 1.0% to 10.0%, chondroitin sulfate in a concentration of from 0.1% to 5.0%, and water, and optionally includes a buffer, an acid or base, a tonicity modulating agent, and/or a free radical scavenger. The pH of such a composition is preferably from 6.0 to 8.0.

In yet another preferred embodiment, the ophthalmic composition consists of glycerol in a concentration of from 0.1% to 5.0%, dextran in a concentration of from 1.0% to 10.0%, chondroitin sulfate in a concentration of from 0.1% to 5.0%, water, a buffer, and a tonicity modulating agent. The pH of such a composition is preferably from 6.0 to 8.0.

In yet a further preferred embodiment, the ophthalmic composition consists of glycerol in a concentration of from 0.1% to 5.0%, dextran in a concentration of from 1.0% to 10.0%, chondroitin sulfate in a concentration of from 0.1% to 5.0%, and water. The pH of such a composition is preferably from 6.0 to 8.0.

The ophthalmic compositions are useful for preventative and therapeutic treatment of numerous ocular conditions and diseases as well as before, during, and after various ocular surgeries, as the compositions provide for ocular surface lubrication, cell membrane stabilization, corneal deturgescence, and, when the ophthalmic compositions contain an antioxidant/free radical scavenger, antioxidant activity. The ophthalmic compositions are useful for protecting the ocular surface (e.g., cornea and conjunctiva), corneal epithelial cells, corneal endothelial cells, and/or other ocular tissues during surgery on an eye. In addition to preventing damage to such ocular tissues during surgery, the ophthalmic compositions may be useful in wound healing after surgery or other events causing injury to the eye. The ophthalmic compositions may also be useful for reducing corneal edema (e.g., during and after corneal transplantation surgery) as well as maintaining corneal deturgescence. The ophthalmic compositions may further be used as a general surgical rinsing solution, especially during ocular surgeries. In addition, the ophthalmic compositions may be useful for rehabilitating stressed or damaged ocular tissue (e.g., an ocular surface) to a normal state (i.e., homeostasis). For example, the ophthalmic compositions may be useful for rehabilitating the ocular surface before and after contact lens wear. Furthermore, the ophthalmic compositions may be useful for maintaining ocular tissue (e.g., an ocular surface) at a normal state (i.e., homeostasis). The ophthalmic compositions may also be useful for enhancing comfort during contact lens wear.

Methods of protecting an animal (e.g., a mammal, especially a human) ocular surface, cornea, corneal epithelial cells, corneal endothelial cells, and/or other ocular tissue comprise administering an effective amount of an ophthalmic composition described herein to the ocular surface, cornea, corneal epithelial cells, corneal endothelial cells, and/or other ocular tissue of a subject. Such administration may occur before and/or during events such as surgery that may cause trauma to the ocular surface, cornea, corneal epithelial cells, corneal endothelial cells, and/or other ocular tissue. The ophthalmic composition preferably maintains contact with the ocular surface, cornea, corneal epithelial cells, corneal endothelial cells, and/or other ocular tissue during the trauma causing event (e.g., surgery).

Methods of treating wounds and/or promoting healing after events causing trauma to an animal (e.g., a mammal, especially a human) ocular surface, cornea, corneal epithelial cells, corneal endothelial cells, and/or other ocular tissue comprise administering an effective amount of an ophthalmic composition described herein to the ocular surface, cornea, corneal epithelial cells, corneal endothelial cells, and/or other ocular tissue of a subject. Such administration may occur before, during, or after events such as surgery that may cause trauma to such ocular tissues, and the ophthalmic composition preferably maintains contact with such ocular tissues after the trauma causing event (e.g., ocular surgery).

Methods of reducing corneal edema comprise administering an effective amount of an ophthalmic composition described herein to an animal (e.g., a mammal, especially a human) cornea of a subject suffering from or susceptible to corneal edema in order to reduce and/or prevent edema in the cornea. Such corneal edema may be caused by an event or disease causing corneal edema such as, for example, corneal transplantation surgery or corneal edema occurring spontaneously. The ophthalmic composition may be administered to the cornea before and/or after edema occurs (e.g., before, during, and/or after corneal transplantation surgery) in order to reduce and/or prevent corneal edema resulting from events such as surgery anticipated to cause such edema.

Methods of rehabilitating stressed or damaged ocular tissue (e.g., an ocular surface) to a normal state (i.e., homeostasis) comprise administering an effective amount of an ophthalmic composition described herein to the stressed or damaged ocular tissue (e.g., ocular surface). In such methods, the stressed or damaged ocular tissue (e.g., ocular surface) is preferably fully rehabilitated, although the ocular tissue may only be partially rehabilitated. Stressed or damaged ocular tissue conditions that may be treated with the ophthalmic compositions include, but are not limited to, dry eye, swollen ocular tissue, excess free radicals, or other conditions stressing or damaging ocular tissue. For example, such a method could be used before and/or after contact lens wear of a subject in order to rehabilitate the ocular surface.

Methods of maintaining ocular tissue (e.g., an ocular surface) at a normal state (i.e., homeostasis) comprise administering an effective amount of an ophthalmic composition described herein to the ocular tissue (e.g., ocular surface). Such a method may be used before, during, or after stress or other damage to the ocular tissue (e.g., ocular surface) such as before, during, and after contact lens wear.

Methods of enhancing comfort during contact lens wear comprise administering an effective amount of an ophthalmic composition described herein to the ocular surface and/or other ocular tissue of a subject wearing one or more contact lenses.

The ophthalmic solutions may be administered as a single dosage, in periodic applications, or may be maintained on the ophthalmic tissue continuously or substantially continuously as appropriate for the particular use. For example, the ophthalmic compositions may be administered once per day in some embodiments, may be administered once every minute for a period of 5 to 10 minutes in other embodiments, and may be administered more or less frequently in yet other embodiments. For methods of maintaining ocular tissue at a normal state as well as in other embodiments of methods of rehabilitating stressed or damaged ocular tissue, an effective amount of the ophthalmic compositions may be applied between 1 to 16 times a day (e.g., from 1 to 8 times a day, from 1 to 6 times a day, or from 1 to 4 times a day), although the ophthalmic compositions may be administered more or less frequently in methods of maintaining ocular tissue as well as in other methods. As will be understood, an effective amount of ophthalmic composition will vary depending upon the particular use, the particular patient and eye the composition is being applied to, and other variable factors. For example, for methods of rehabilitating stressed or damaged ocular tissue, two or three drops of the ophthalmic composition may be used immediately after an insult and could be administered every minute (or other interval) for a period thereafter, although other amounts of ophthalmic compositions could be used in more or less frequency.

Any effective method may be used to produce the ophthalmic compositions described herein. An example of a method for making an ophthalmic composition using a borate buffer follows:

1. Add to the manufacturing vessel 80% of the batch quantity of Purified Water.
2. Heat to 85-90° C.
3. While mixing, add the batch quantity of Dextran-40K. Make sure powder is not splashed on vessel wall above the water level.
4. Mix until all Dextran is dissolved and a clear solution is observed.
5. Discontinue heating and allow solution to start cooling.
6. While cooling, increase speed of mixer and add slowly and to vortex the batch quantity of Chondroitin Sulfate Sodium. Avoid formation of undissolved lumps. Mix until all is dissolved.
7. Add batch quantity of Glycerol. Rinse container with few milliliters of Purified Water and add to the manufacturing vessel to assure complete transfer of glycerol.
8. Add batch quantity of Boric Acid. Mix to dissolve.
9. Add batch quantity of Sodium Borate (decahydrate). Mix to dissolve
10. Qs with Purified Water. Mix to homogeneity.
11. Using appropriate filters (e.g. 5 to 25 micron filters) filter the solution to remove any undissolved particles.
12. Sterile filter through 0.20 micron filters.

EXAMPLES

The invention will be further explained by the following illustrative examples that are intended to be non-limiting.

Example 1

Four different formulations of the ophthalmic compositions described herein were prepared and the comfort of such formulations was compared to Systane® lubricant eye drops, which contain polyethylene glycol 400, propylene glycol, and HP-guar. The four formulations of the ophthalmic compositions (designated as Cla-022, Cla-026, Cla-028, and Cla-030) that were prepared are listed below in Table I:

TABLE I

|  | Cla-022 | Cla-026 | Cla-028 | Cla-030 |
| --- | --- | --- | --- | --- |
| Glycerol (percent, weight/volume) | 1.0 | 1.0 | 1.0 | 1.0 |
| Chondroitin sulfate (percent, weight/volume) | 2.5 | 2.5 | 2.5 | 2.5 |
| Dextran, 40,000 (percent, weight/volume) | 5.0 | 5.0 | 2.5 | 1.0 |
| Boric Acid (percent, weight/volume) | 0.5 | 0.5 | 0.5 | 0.5 |
| Sodium borate (percent, weight/volume) | 0.18 | 0.18 | 0.18 | 0.18 |
| Sodium chloride (percent, weight/volume) | 0 | 0.25 | 0.25 | 0.25 |
| Purified water | balance | balance | balance | balance |

Four blinded tests were conducted in order to compare the comfort level of the different test formulations to the comfort of Systane® lubricant eye drops. In each test, the Systane® lubricant eye drops were tested against one of the four formulations. At three time points over a 24 hour period (8 am, 12 pm, and 5 pm), each human subject received one drop of one of the two compositions in the right eye and received a drop of the other composition in the left eye, but the subjects were not informed of the identity of the compositions. The composition administered to each eye remained constant during the test period (i.e., the same composition was applied to the same eye at each time point of application). At various time points discussed below, the subject indicated the comfort of each eye on a scale of 1-10, with 10 being the most comfortable. The subject gave comfort ratings at each of the following time points:

| Day 1 | |
| --- | --- |
| 8 am | (1) immediately upon administration, and (2) two minutes after administration; |
| Noon | (1) pre-administration, (2) immediately upon administration, and (3) two minutes after administration; |
| 5 pm | (1) pre-administration, (2) immediately upon administration, and (3) two minutes after administration; |
| Bedtime | (1) at bedtime for subject; |
| Day 2 | |
| 8 am | (1) at 8am. |

The results of each of the four tests on the comfort of the formulations (Cla-022, Cla-026, Cla-028, Cla-030) as compared to Systane® lubricant eye drops (Sys) are shown below in Tables II-V.

TABLE IIa

Cla-022 v. Systane: Day 1, 8 am-12 pm

| Subject | 8 am-admin. Sys | 8 am-admin. Cla-022 | 8 am-2 min. after admin. Sys | 8 am-2 min. after admin. Cla-022 | 12 pm Pre-admin. Sys | 12 pm Pre-admin. Cla-022 | 12 pm-Admin Sys | 12 pm-Admin Cla-022 | 12 pm-2 min. after admin. Sys | 12 pm-2 min. after admin. Cla-022 |
|---|---|---|---|---|---|---|---|---|---|---|
| A | 10 | 10 | 9 | 10 | 5 | 6 | 8 | 8 | 8 | 8 |
| B | 8 | 6 | 5 | 7 | 8 | 8 | 9 | 6 | 7 | 7 |
| C | 9 | 6 | 9 | 6 | 9 | 7 | 9 | 7 | 8 | 8 |
| D | 10 | 9 | 10 | 9 | 10 | 10 | 8 | 10 | 10 | 9 |
| E | 10 | 10 | 9 | 10 | 10 | 10 | 10 | 10 | 9 | 9 |
| F | 9 | 9 | 9 | 9 | 10 | 10 | 9 | 9 | 9 | 9 |
| G | 8 | 3 | 8 | 6 | 7 | 8 | 2 | 8 | 4 | 8 |
| H | 9 | 9 | 9 | 9 | 10 | 10 | 9 | 10 | 9 | 9 |
| I | 9 | 7 | 9 | 4 | 7 | 8 | 6 | 5 | 6 | 6 |
| J | 9 | 9 | 9 | 9 | 10 | 10 | 10 | 7 | 10 | 9 |
| K | 10 | 8 | 10 | 9 | 9 | 9 | 8 | 8 | 9 | 9 |
| L | 8 | 7 | 9 | 9 | 8 | 8 | 8 | 7 | 8 | 7 |
| M | 8 | 6 | 8 | 6 | 8 | 8 | 7 | 6 | 7 | 6 |
| N | 9 | 9 | 7 | 9 | 9 | 9 | 8 | 8 | 7 | 9 |
| Avg Score | 9.0000 | 7.7143 | 8.5714 | 8.0000 | 8.5714 | 8.6429 | 7.9286 | 7.7857 | 7.9286 | 8.0714 |

TABLE IIb

Cla-022 v. Systane: Day 1, 5 pm-Day 2, 8 am

| Subject | 5 pm-Pre-admin. Sys | 5 pm-Pre-admin. Cla-022 | 5 pm-Admin. Sys | 5 pm-Admin. Cla-022 | 5 pm-2 min. after admin. Sys | 5 pm-2 min. after admin. Cla-022 | Bedtime Sys | Bedtime Cla-022 | Day 2-8 am Sys | Day 2-8 am Cla-022 |
|---|---|---|---|---|---|---|---|---|---|---|
| A | 6 | 5 | 7 | 7 | 7 | 7 | 7 | 7 | 7 | 7 |
| B | 2 | 3 | 5 | 7 | 8 | 8 | 3 | 3 | 5 | 5 |
| C | 9 | 9 | 9 | 9 | 9 | 9 | 9 | 9 | 9 | 9 |
| D | 10 | 10 | 10 | 7 | 10 | 7 | 9 | 9 | 9 | 8 |
| E | 9 | 8 | 9 | 8 | 8 | 8 | 10 | 10 | 10 | 10 |
| F | 9 | 9 | 8 | 7 | 9 | 9 | 9 | 9 | 10 | 10 |
| G | 5 | 9 | 8 | 2 | 8 | 3 | 9 | 9 | 9 | 4 |
| H | 10 | 10 | 10 | 9 | 9 | 10 | 10 | 10 | 10 | 10 |
| I | 6 | 7 | 5.5 | 6.5 | 6 | 6.5 | 7 | 8 | 8 | 8 |
| J | 10 | 10 | 10 | 10 | 10 | 10 | 10 | 10 | 10 | 10 |
| K | 8 | 8 | 8 | 8 | 9 | 9 | 9 | 9 | 9 | 9 |
| L | 7 | 7 | 8 | 7 | 8 | 8 | 8 | 8 | 8 | 8 |
| M | 7 | 7 | 8 | 6 | 8 | 6 | 7 | 7 | 7 | 7 |
| N | 8 | 8 | 8 | 8 | 6 | 8 | 8 | 8 | 8 | 8 |
| Avg Score | 7.5714 | 7.8571 | 8.1071 | 7.2500 | 8.2143 | 7.7500 | 8.2143 | 8.2857 | 8.5000 | 8.0714 |

TABLE IIIa

Cla-026 v. Systane: Day 1, 8 am-12 pm

| Subject | 8 am-admin. Sys | 8 am-admin. Cla-026 | 8 am-2 min. after admin. Sys | 8 am-2 min. after admin. Cla-026 | 12 pm Pre-admin. Sys | 12 pm Pre-admin. Cla-026 | 12 pm-Admin Sys | 12 pm-Admin Cla-026 | 12 pm-2 min. after admin. Sys | 12 pm-2 min. after admin. Cla-026 |
|---|---|---|---|---|---|---|---|---|---|---|
| A | 10 | 10 | 10 | 10 | 7 | 7 | 10 | 10 | 10 | 10 |
| B | 10 | 7 | 8 | 6 | 10 | 7 | 6 | 4 | 3 | 7 |
| C | 7 | 7 | 9 | 8 | 6 | 6 | 7 | 7 | 9 | 9 |
| D | 9 | 9 | 10 | 10 | 10 | 10 | 10 | 10 | 10 | 10 |
| E | 10 | 10 | 8 | 9 | 9 | 9 | 9 | 9 | 8 | 8 |
| F | 9 | 9 | 9 | 9 | 10 | 10 | 6 | 8 | 9 | 9 |

TABLE IIIa-continued

Cla-026 v. Systane: Day 1, 8 am-12 pm

| Subject | 8 am-admin. | | 8 am-2 min. after admin. | | 12 pm Pre-admin. | | 12 pm-Admin | | 12 pm-2 min. after admin. | |
|---|---|---|---|---|---|---|---|---|---|---|
| | Sys | Cla-026 | Sys | Cla-026 | Sys | Cla-026 | Sys | Cla-026 | Sys | Cla-026 |
| G | 7 | 4 | 3 | 8 | 8 | 5 | 7 | 3 | 3 | 8 |
| H | 10 | 10 | 10 | 10 | 10 | 10 | 10 | 9 | 10 | 9 |
| I | 7 | 8 | 7.5 | 7.5 | 8 | 7 | 7 | 7 | 7 | 6 |
| J | 10 | 10 | 7 | 8 | 8 | 10 | 9 | 10 | 9 | 9 |
| K | 8 | 9 | 9 | 9 | 9 | 9 | 8 | 8 | 9 | 9 |
| L | 8 | 8 | 9 | 9 | 8 | 8 | 9 | 9 | 9 | 9 |
| M | 7 | 8 | 6 | 7 | 6 | 7 | 7 | 7 | 6 | 6 |
| N | 10 | 9 | 10 | 8 | 10 | 9 | 10 | 7 | 10 | 5 |
| Avg Score | 8.7143 | 8.4286 | 8.2500 | 8.4643 | 8.5000 | 8.1429 | 8.2143 | 7.7143 | 8.0000 | 8.1429 |

TABLE IIIb

Cla-026 v. Systane: Day 1, 5 pm-Day 2, 8 am

| Subject | 5 pm-Pre-admin. | | 5 pm-Admin. | | 5 pm-2 min. after admin. | | Bedtime | | Day 2-8 am | |
|---|---|---|---|---|---|---|---|---|---|---|
| | Sys | Cla-026 | Sys | Cla-026 | Sys | Cla-026 | Sys | Cla-026 | Sys | Cla-026 |
| A | 6 | 6 | 10 | 10 | 9 | 10 | 9 | 9 | 7 | 7 |
| B | 1 | 2 | 4 | 3 | 3 | 5 | 3 | 3 | 5 | 5 |
| C | 7 | 7 | 8 | 9 | 9 | 9 | 6 | 6 | 8 | 8 |
| D | 10 | 10 | 10 | 10 | 10 | 10 | 10 | 10 | 10 | 10 |
| E | 9 | 10 | 8 | 9 | 10 | 9 | 9 | 9 | 10 | 10 |
| F | 8 | 8 | 9 | 9 | 9 | 9 | | | | |
| G | 7 | 9 | 7 | 4 | 3 | 8 | 8 | 8 | 10 | 10 |
| H | 10 | 10 | 10 | 10 | 10 | 10 | 10 | 10 | 10 | 10 |
| I | 6.5 | 6 | 6 | 5 | 6 | 4 | 8 | 8 | 8 | 8 |
| J | 8 | 9 | 9 | 9 | 8 | 9 | 8 | 7 | 9 | 9 |
| K | 9 | 9 | 9 | 9 | 9 | 9 | 9 | 9 | 9 | 9 |
| L | 7 | 7 | 8 | 8 | 8 | 8 | 8 | 8 | 8 | 8 |
| M | 5 | 5 | 7 | 8 | 7 | 7 | 7 | 8 | 7 | 8 |
| N | 8 | 8 | 8 | 7 | 8 | 5 | 8 | 6 | 9 | 9 |
| Avg Score | 7.2500 | 7.5714 | 8.0714 | 7.8571 | 7.7857 | 8.0000 | 7.3571 | 7.2143 | 7.8571 | 7.9286 |

TABLE IVa

Cla-028 v. Systane: Day 1, 8 am-12 pm

| Subject | 8 am-2 min. | | 8 am-admin. after admin. | | 12 pm Pre-admin. | | 12 pm-Admin | | 12 pm-2 min. after admin. | |
|---|---|---|---|---|---|---|---|---|---|---|
| | Sys | Cla-028 | Sys | Cla-028 | Sys | Cla-028 | Sys | Cla-028 | Sys | Cla-028 |
| A | 10 | 10 | 10 | 10 | 10 | 6 | 9 | 9 | 9 | 9 |
| B | 9 | 7 | 9 | 7 | 10 | 7 | 6 | 8 | 5 | 9 |
| C | 8 | 7 | 7 | 6 | 8 | 8 | 7 | 7 | 8 | 8 |
| D | 10 | 9 | 10 | 10 | 10 | 10 | 10 | 10 | 10 | 10 |
| E | 10 | 8 | 10 | 8 | 10 | 10 | 10 | 10 | 8 | 9 |
| F | 6 | 7 | 8 | 9 | 9 | 9 | 6 | 6 | 8 | 8 |
| G | 8 | 8 | 6 | 8 | 10 | 10 | 8 | 8 | 8 | 5 |
| H | 10 | 10 | 9 | 9 | 10 | 10 | 10 | 10 | 9 | 10 |
| I | 8 | 8 | 8 | 7 | 10 | 10 | 9 | 10 | 9.5 | 9.5 |
| J | 10 | 9 | 9 | 9 | 8 | 5 | 9 | 9 | 9 | 7 |
| K | 8 | 8 | 8 | 8 | 10 | 10 | 8 | 8 | 9 | 9 |
| L | 10 | 10 | 10 | 10 | 8 | 8 | 10 | 9 | 10 | 9 |
| M | 9 | 9 | 9 | 8 | 9 | 9 | 9 | 8 | 9 | 8 |
| N | 10 | 10 | 10 | 7 | 10 | 10 | 10 | 10 | 10 | 7 |
| Avg Score | 9.0000 | 8.5714 | 8.7857 | 8.2857 | 9.4286 | 8.7143 | 8.6429 | 8.7143 | 8.6786 | 8.3929 |

TABLE IVb

Cla-028 v. Systane: Day 1, 5 pm-Day 2, 8 am

| Subject | 5 pm-Pre-admin. | | 5 pm-Admin. | | 5 pm-2 min. after admin. | | Bedtime | | Day 2-8 am | |
| --- | --- | --- | --- | --- | --- | --- | --- | --- | --- | --- |
| | Sys | Cla-028 | Sys | Cla-028 | Sys | Cla-028 | Sys | Cla-028 | Sys | Cla-028 |
| A | 6 | 6 | 9 | 9 | 8 | 8 | 8 | 8 | 7 | 7 |
| B | 8 | 10 | 5 | 6 | 6 | 8 | 10 | 10 | 10 | 10 |
| C | 8 | 8 | 8 | 7 | 9 | 7 | 8 | 8 | 8 | 7 |
| D | 10 | 10 | 9 | 9 | 10 | 10 | 10 | 10 | 9 | 9 |
| E | 10 | 10 | 10 | 10 | 9 | 8 | 9 | 9 | 10 | 10 |
| F | 10 | 10 | 8 | 8 | 9 | 9 | 9 | 9 | 9 | 9 |
| G | 10 | 10 | 8 | 6 | 9 | 8 | 10 | 10 | 10 | 10 |
| H | 10 | 10 | 10 | 10 | 10 | 10 | 10 | 10 | 10 | 10 |
| I | 8 | 8 | 9 | 9 | 8 | 8 | 8 | 8 | 10 | 10 |
| J | 8 | 7 | 10 | 9 | 9 | 8 | 6 | 4 | 9 | 8 |
| K | 9 | 9 | 8 | 8 | 9 | 9 | 8 | 8 | 9 | 9 |
| L | 8 | 8 | 8 | 8 | 9 | 9 | 8 | 8 | 8 | 8 |
| M | 9 | 9 | 9 | 9 | 8 | 8 | 8 | 8 | 8 | 8 |
| N | 10 | 10 | 10 | 8 | 9 | 8 | 10 | 10 | 10 | 10 |
| Avg Score | 8.8571 | 8.9286 | 8.6429 | 8.2857 | 8.7143 | 8.4286 | 8.7143 | 8.5714 | 9.0714 | 8.9286 |

TABLE Va

Cla-030 v. Systane: Day 1, 8 am-12 pm

| Subject | 8 am-admin. | | 8 am-2 min. after admin. | | 12 pm Pre-admin. | | 12 pm-Admin | | 12 pm-2 min. after admin. | |
| --- | --- | --- | --- | --- | --- | --- | --- | --- | --- | --- |
| | Sys | Cla-030 | Sys | Cla-030 | Sys | Cla-030 | Sys | Cla-030 | Sys | Cla-030 |
| A | 10 | 10 | 10 | 10 | 8 | 7 | 10 | 9 | 9 | 10 |
| B | 9 | 5 | 9 | 9 | 9 | 8 | 9 | 9 | 10 | 10 |
| C | 7 | 9 | 8 | 9 | 6 | 9 | 7 | 7 | 9 | 9 |
| D | 9 | 10 | 10 | 10 | 9 | 9 | 10 | 9 | 10 | 9 |
| E | 10 | 10 | 9 | 9 | 10 | 10 | 10 | 10 | 9 | 9 |
| F | 7 | 7 | 9 | 9 | 9 | 9 | 8 | 8 | 9 | 9 |
| G | 8 | 6 | 6 | 8 | 10 | 10 | 7 | 7 | 8 | 8 |
| H | 10 | 9 | 10 | 9 | 10 | 10 | 10 | 10 | 8 | 10 |
| I | 7 | 7.5 | 7 | 9 | 9 | 9 | 8 | 7 | 8 | 8 |
| J | 10 | 10 | 10 | 9 | 7 | 8 | 10 | 6 | 10 | 8 |
| K | 9 | 9 | 9 | 8 | 9 | 9 | 9 | 9 | 9 | 9 |
| L | 7 | 7 | 9 | 9 | 8 | 8 | 8 | 8 | 8 | 8 |
| M | 8 | 7 | 8 | 7 | 7 | 7 | 8 | 8 | 7 | 7 |
| N | 10 | 10 | 10 | 10 | 10 | 10 | 10 | 10 | 10 | 9.5 |
| Avg Score | 8.6429 | 8.3214 | 8.7857 | 8.9286 | 8.6429 | 8.7857 | 8.8571 | 8.3571 | 8.8571 | 8.8214 |

TABLE Vb

Cla-030 v. Systane: Day 1, 5 pm-Day 2, 8 am

| Subject | 5 pm-Pre-admin. | | 5 pm-Admin. | | 5 pm-2 min. after admin. | | Bedtime | | Day 2-8 am | |
| --- | --- | --- | --- | --- | --- | --- | --- | --- | --- | --- |
| | Sys | Cla-030 | Sys | Cla-030 | Sys | Cla-030 | Sys | Cla-030 | Sys | Cla-030 |
| A | 8 | 8 | 10 | 10 | 9 | 9 | 9 | 9 | 8 | 8 |
| B | 7 | 10 | 9 | 7 | 9 | 7 | 9 | 5 | 10 | 7 |
| C | 7 | 7 | 7 | 7 | 9 | 9 | 7 | 7 | 9 | 9 |
| D | 9 | 9 | 9 | 10 | 10 | 10 | 9 | 9 | 8 | 8 |
| E | 9 | 9 | 9 | 9 | 9 | 9 | 9 | 9 | 10 | 10 |
| F | 10 | 10 | 9 | 9 | 10 | 10 | 9 | 9 | 9 | 9 |
| G | 10 | 10 | 8 | 6 | 9 | 8 | 2 | 5 | 4 | 8 |
| H | 10 | 10 | 8 | 10 | 10 | 10 | 10 | 10 | 10 | 10 |
| I | 7 | 7 | 6.5 | 7 | 6.5 | 7 | 9 | 9 | 10 | 10 |
| J | 8 | 8 | 10 | 7 | 9 | 8 | 6 | 3 | 9 | 8 |
| K | 9 | 9 | 9 | 9 | 9 | 9 | 8 | 8 | 9 | 9 |
| L | 6 | 7 | 7 | 7 | 7 | 7 | 8 | 8 | 8 | 8 |

TABLE Vb-continued

Cla-030 v. Systane: Day 1, 5 pm-Day 2, 8 am

| Subject | 5 pm-Pre-admin. | | 5 pm-Admin. | | 5 pm-2 min. after admin. | | Bedtime | | Day 2-8 am | |
|---|---|---|---|---|---|---|---|---|---|---|
| | Sys | Cla-030 | Sys | Cla-030 | Sys | Cla-030 | Sys | Cla-030 | Sys | Cla-030 |
| M | 6 | 7 | 8 | 8 | 8 | 7 | 6 | 7 | 6 | 7 |
| N | 10 | 10 | 8 | 8 | 7 | 7 | 9 | 9 | 9 | 9 |
| Avg Score | 8.2857 | 8.6429 | 8.3929 | 8.1429 | 8.6786 | 8.3571 | 7.8571 | 7.6429 | 8.5000 | 8.5714 |

Example 2

One unbuffered formulation, one phosphate buffered formulation, and one borate buffered formulation of the ophthalmic compositions described herein were prepared as described in Table VI below. The borate buffered formulation did not require any pH adjustment, as its natural pH was 7.4.

TABLE VI

| Ingredient | Unbuffered Solution Percent (wt/vol) | Borate Buffer Percent (wt/vol) | Phosphate Buffer Percent (wt/vol) |
|---|---|---|---|
| Glycerol | 1.0 | 1.0 | 1.0 |
| Chondroitin Sulfate | 2.5 | 2.5 | 2.5 |
| Dextran-40 | 5.0 | 5.0 | 5.0 |
| Sodium Chloride | 0.3 | — | 0.3 |
| NaOH or HCl | To adjust pH to 7.4 | None required | To adjust pH to 7.4 |
| Boric Acid | — | 0.5 | — |
| Sodium Borate | — | 0.18 | — |
| Phophate buffer 0.005M | — | — | q.s. to 100 |
| Purified Water | q.s. to 100 | q.s. to 100 | q.s. to 100 |

In order to evaluate the comfort of the solutions, blinded tests were conducted on a group of 16 human subjects. In each test, one drop of one of the buffered formulations was instilled in one eye of a subject and one drop of the unbuffered formulation was instilled in the contralateral eye of the subject. Comfort was evaluated immediately after instillation of the drops and 2 minutes post instillation; the subject indicated the comfort of each eye on a scale of 1-10, with 10 being the most comfortable. The study was repeated the next day using the other buffered formulation in one eye and the unbuffered formulation in the contralateral eye. Both study director and subjects were masked.

The average comfort scores for each of the formulations are shown in Table VII below:

TABLE VII

| Unbuffered Solution | | Borate Buffer | | Unbuffered Solution | | Phosphate Buffer | |
|---|---|---|---|---|---|---|---|
| Immediate | 2 min | Immediate | 2 min | Immediate | 2 min | Immediate | 2 min |
| 8.906 | 9.031 | 8.844 | 9.000 | 8.656 | 9.094 | 8.938 | 8.875 |

While the invention has been described in detail and with reference to specific embodiments thereof, it will be apparent to one skilled in the art that various changes and modifications can be made without departing from the spirit and scope of the invention.

What is claimed is:

1. An ophthalmic composition consisting essentially of:
   glycerol in a concentration of from 0.1% to 5.0%;
   dextran in a concentration of from 1.0% to 10.0%;
   chondroitin sulfate in a concentration of from 0.1% to 5.0%; and
   water.

2. The ophthalmic composition of claim 1, wherein glycerol is present in a concentration of from 0.3% to 1.7%, dextran is present in a concentration of from 3.0% to 7.0%, and chondroitin sulfate is present in a concentration of from 0.5% to 4.5%.

3. The ophthalmic composition of claim 1, wherein glycerol is present in a concentration of from 0.6% to 1.4%, dextran is present in a concentration of from 4.0% to 6.0%, and chondroitin sulfate is present in a concentration of from 1.5% to 3.5%.

4. The ophthalmic composition of claim 1, wherein glycerol is present in a concentration of from 0.8% to 1.2%, dextran is present in a concentration of from 4.5% to 5.5%, and chondroitin sulfate is present in a concentration of from 2.0% to 3.0%.

5. The ophthalmic composition of claim 4, wherein chondroitin sulfate is present in a concentration of from 2.3% to 2.7%.

6. The ophthalmic composition of claim 1, wherein glycerol is present in a concentration of 1.0%, dextran is present in a concentration of 5.0%, and chondroitin sulfate is present in a concentration of 2.5%.

7. An ophthalmic composition consisting essentially of:
   glycerol in a concentration of from 0.1% to 5.0%;
   dextran in a concentration of from 1.0% to 10.0%;
   chondroitin sulfate in a concentration of from 0.1% to 5.0%;
   water;
   a buffer; and
   pH 6 to 8.

8. The ophthalmic composition of claim 7, wherein the pH of the composition is from 7.0 to 7.4.

9. The ophthalmic composition of claim 7, wherein glycerol is present in a concentration of from 0.3% to 1.7%, dextran is present in a concentration of from 3.0% to 7.0%, and chondroitin sulfate is present in a concentration of from 0.5% to 4.5%.

10. The ophthalmic composition of claim 7, wherein glycerol is present in a concentration of from 0.6% to 1.4%, dextran is present in a concentration of from 4.0% to 6.0%, and chondroitin sulfate is present in a concentration of from 1.5% to 3.5%.

11. The ophthalmic composition of claim 7, wherein glycerol is present in a concentration of from 0.8% to 1.2%, dextran is present in a concentration of from 4.5% to 5.5%, and chondroitin sulfate is present in a concentration of from 2.0% to 3.0%.

12. The ophthalmic composition of claim 11, wherein chondroitin sulfate is present in a concentration of from 2.3% to 2.7%.

13. The ophthalmic composition of claim 7, wherein glycerol is present in a concentration of 1.0%, dextran is present in a concentration of 5.0%, and chondroitin sulfate is present in a concentration of 2.5%.

14. The ophthalmic composition of claim 7, wherein the buffer is sodium borate and boric acid.

15. An ophthalmic composition consisting of glycerol in a concentration of from 0.1% to 5.0%;
dextran in a concentration of from 1.0% to 10.0%;
chondroitin sulfate in a concentration of from 0.1% to 5.0%; and
water.

16. The ophthalmic composition of claim 15, wherein glycerol is present in a concentration of from 0.3% to 1.7%, dextran is present in a concentration of from 3.0% to 7.0%, and chondroitin sulfate is present in a concentration of from 0.5% to 4.5%.

17. The ophthalmic composition of claim 15, wherein glycerol is present in a concentration of from 0.6% to 1.4%, dextran is present in a concentration of from 4.0% to 6.0%, and chondroitin sulfate is present in a concentration of from 1.5% to 3.5%.

18. The ophthalmic composition of claim 15, wherein glycerol is present in a concentration of from 0.8% to 1.2%, dextran is present in a concentration of from 4.5% to 5.5%, and chondroitin sulfate is present in a concentration of from 2.0% to 3.0%.

19. The ophthalmic composition of claim 18, wherein chondroitin sulfate is present in a concentration of from 2.3% to 2.7%.

20. The ophthalmic composition of claim 15, wherein glycerol is present in a concentration of 1.0%, dextran is present in a concentration of 5.0%, and chondroitin sulfate is present in a concentration of 2.5%.

\* \* \* \* \*

UNITED STATES PATENT AND TRADEMARK OFFICE
CERTIFICATE OF CORRECTION

PATENT NO. : 7,820,639 B2 Page 1 of 1
APPLICATION NO. : 11/240000
DATED : October 26, 2010
INVENTOR(S) : Richard L. Lindstrom It is certified that error appears in the above-identified patent and that said Letters Patent is hereby corrected as shown below:

On the Title Page, Item (76) under "Inventor:" - please correct the inventor's zip code to read "55391."

Signed and Sealed this

Fourteenth Day of December, 2010

David J. Kappos
*Director of the United States Patent and Trademark Office*